United States Patent [19]

Skuballa et al.

[11] Patent Number: 4,560,786
[45] Date of Patent: Dec. 24, 1985

[54] Δ$^{8,9}$-PROSTAGLANDIN DERIVATIVES, THEIR PREPARATION AND USE AS MEDICINAL AGENTS

[75] Inventors: Werner Skuballa; Bernd Raduechel; Norbert Schwarz; Helmut Vorbrueggen; Walter Elger; Olaf Loge; Michael-Harold Town, all of Berlin, Fed. Rep. of Germany

[73] Assignee: Schering Aktiengesellschaft, Berlin and Bergkamen, Fed. Rep. of Germany

[21] Appl. No.: 391,734

[22] Filed: Jun. 24, 1982

[30] Foreign Application Priority Data

Jun. 24, 1981 [DE] Fed. Rep. of Germany ....... 3125271

[51] Int. Cl.$^4$ .......................................... C07C 177/00
[52] U.S. Cl. ..................... 560/55; 560/121; 562/472; 562/503; 564/80; 564/89; 564/171; 564/174; 564/189; 568/657; 568/812; 568/813; 549/415; 514/530
[58] Field of Search .................. 560/55, 121; 562/472, 562/503; 564/80, 89, 171, 174, 189; 568/657, 812, 813; 549/415; 514/530

[56] References Cited

FOREIGN PATENT DOCUMENTS 7354134  7/1980  France ................................ 560/55

OTHER PUBLICATIONS

Ermili et al., Il Farmaco, vol. 31, No. 9, Sep. 1976, pp. 649-654.

Primary Examiner—Paul J. Killos
Attorney, Agent, or Firm—Millen & White

[57] ABSTRACT

Δ$^{8,9}$-Prostane derivatives of Formula I

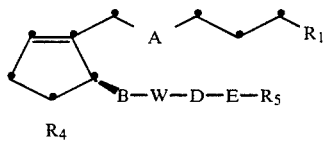

wherein
R$_1$ is CH$_2$OH or

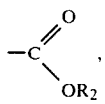

wherein R$_2$ is hydrogen, alkyl, cycloalkyl, aryl, or a heterocyclic residue; or R$_1$ is

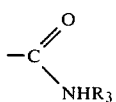

wherein R$_3$ is an acid residue or R$_2$;
A is —CH$_2$—CH$_2$— or cis—CH=CH;
B is —CH$_2$—CH$_2$—, trans—CH=CH— or —C≡C—
W is a free or functionally modified hydroxymethylene group or free or functionally modified

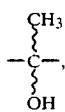

wherein the OH—group can be in the α— or β— position;
D and E jointly are a direct bond or
D is straight chain or branched alkylene or alkenylene of 1-10 carbon atoms which can optionally be substituted by fluorine atoms, and E is oxygen, sulfur, a direct bond, —C≡C— or —CR$_6$=CR$_7$—, wherein R$_6$ and R$_7$ differ from each other and each is hydrogen, chlorine or alkyl;
R$_4$ is free or functionally modified hydroxy and
R$_5$ is an optionally substituted aliphatic group, cycloalkyl, optionally substituted aryl, or a heterocyclic group, and when R$_2$ is hydrogen, physiologically compatible salts thereof with bases,
have valuable pharmacological properties, e.g. luteolytic and abortifacient activities.

46 Claims, No Drawings

$\Delta^{8,9}$-PROSTAGLANDIN DERIVATIVES, THEIR PREPARATION AND USE AS MEDICINAL AGENTS

BACKGROUND OF THE INVENTION

The present invention relates to novel $\Delta^{8,9}$-prostaglandin derivatives, a process for their preparation, and their use as medicinal agents.

It is known from the voluminous state of the art of the prostaglandins and their analogs that this class of compounds, due to their biological and pharmacological properties, is suitable for the treatment of mammals, including man. Their use as medicines, however, frequently presents difficulties. Most of the natural prostaglandins have a period of efficacy too brief for therapeutic purposes, since they are metabolically broken down too rapidly by various enzymatic processes. All structural modifications aim at raising their duration of effectiveness and selectivity of efficacy.

It has been discovered that these novel $\Delta^{8,9}$-prostaglandin derivatives possess a pronounced specificity of effectiveness, improved efficacy, and longer duration of activity than natural prostaglandins, and that they are especially suitable for oral administration. The novel $\Delta^{8,9}$-prostaglandins are also chemically stable.

SUMMARY OF THE INVENTION

It is an object of this invention to provide new prostaglandin analogs which have improved properties, e.g., those discussed above.

Upon further study of the specification and appended claims, further objects and advantages of this invention will become apparent to those skilled in the art.

These objects have been acheived by this invention by providing $\Delta^{8,9}$-prostane derivatives of Formula I

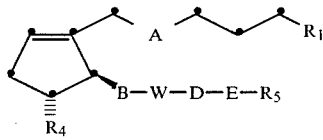

wherein
$R_1$ is CH$_2$OH or

wherein $R_2$ is hydrogen, alkyl, cycloalkyl, aryl, or a heterocyclic residue, or $R_1$ is

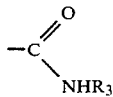

wherein $R_3$ is an acid residue or $R_2$;
A is —CH$_2$—CH$_2$— or cis—CH=CH—;
B is —CH$_2$—CH$_2$—, trans—CH=CH— or —C≡C—;
W is a free or functionally modified hydroxymethylene group or free or functionally modified

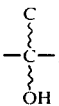

wherein the OH— group can be in the $\alpha$ or $\beta$-position;
D and E jointly are a direct bond or
D is straight chain or branched alkylene or alkenylene of 1-10 carbon atoms which can optionally be substituted by fluorine atoms, and E is oxygen, sulfur, a direct bond, —C≡C— or —CR$_6$=CR$_7$—, wherein R$_6$ and R$_7$ differ from each other and each is hydrogen, chlorine or alkyl;
$R_4$ is a free or functionally modified hydroxy group; and
$R_5$ is an optionally substituted aliphatic group, e.g., alkyl or halosubstituted alkyl, cycloalkyl, optionally substituted aryl, or a heterocyclic group; and, when R$_2$ is hydrogen, the physiologically compatible salts thereof with bases.

It has been discovered that these novel $\Delta^{8,9}$-prostaglandin derivatives possess a pronounced specificity of effectiveness, improved efficacy, and longer duration of activity than natural prostaglandins, and that they are especially suitable for oral administration. The novel $\Delta^{8,9}$-prostaglandins are also chemically stable.

DETAILED DISCUSSION

Suitable alkyl groups $R_2$ are linear or branched alkyl groups of 1–10 carbon atoms, e.g. methyl, ethyl, propyl, butyl, isobutyl, tert-butyl, pentyl, neopentyl, hexyl, heptyl, decyl, etc. The alkyl groups $R_2$ can optionally be mono- to polysubstituted by halogen atoms (F,Cl,Br) alkoxy groups, optionally substituted aryl or aroyl wherein the aryl portion and the substituents are as defined below for the corresponding $R_2$ groups per se, di-C$_{1-4}$-alkylamino, and tri-C$_{1-4}$-alkylammonium. Single substitution is preferred. Examples of such substituents include fluorine, chlorine, bromine, phenyl, dimethylamino, diethylamino, methoxy, ethoxy etc. Preferred alkyl groups $R_2$ are those of 1–4 carbon atoms, such as, for example methyl, ethyl, propyl, dimethylaminopropyl, isobutyl or butyl.

Suitable aryl or aroyl groups $R_2$ can be substituted or unsubstituted. Examples include phenyl, 1-naphthyl, and 2-naphthyl, each of which can be substituted by 1–3 halogen atoms, phenyl, 1–3 alkyl groups of 1–4 carbon atoms each, or a chloromethyl, fluoromethyl, trifluoromethyl, carboxy, hydroxy, or alkoxy group of 1–4 carbon atoms. Substitution in the 3- and 4-position on the phenyl ring is preferred, e.g. by fluorine, chlorine, alkoxy, or trifluoromethyl, or in the 4-position by hydroxy.

Suitable cycoalkyl groups $R_2$ can contain 3–10, preferably 5 or 6 carbon atoms in the ring. The rings can be substituted by alkyl groups of 1–4 carbon atoms. Examples include cyclopentyl, cyclohexyl, methylcyclohexyl, and adamantyl.

Suitable heterocyclic groups $R_2$ include 5- and 6-membered heterocycles, containing at least one hetero atom, preferably nitrogen, oxygen, or sulfur and preferably aromatic monocycles, the remaining atoms being carbonatoms. Examples include: 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, and others.

Suitable acid residues $R_3$ are physiologically compatible acid residues which produce physiologically compatible compounds. Preferred acids are organic carboxylic acids and sulfonic acids of 1–15 carbon atoms pertaining to the aliphatic, cycloaliphatic, aromatic, aromaticaliphatic, and heterocyclic series. The acids are usually hydrocarbons but the heterocyclic and other non-hydrocarbon acids are fully equivalent as are the substituted analogs of all of these. These acids can be saturated, unsaturated and/or polybasic and/or substituted in the usual way. Examples of substituents include alkyl, hydroxy, alkoxy, oxo, or amino groups or halogen atoms. The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecyclic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acids, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid etc. Especially preferred acyl residues are those of up to 10 carbon atoms. Examples of suitable sulfonic acids include methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

The hydroxy groups in W and $R_4$ can be functionally modified, for example by etherifying or esterifying them; the modified hydroxy group in W can likewise be in the α- or β-position.

Suitable ether and acyl residues are well known to persons skilled in the art. Ether residues which can be readily split off are preferred and include e.g. tetrahydropyranyl, tetrahydrofuranyl, α-ethoxyethyl, trimethylsilyl, dimethylsilyl, tert-butylsilyl, and tribenzylsilyl residues. Suitable acyl residues are those described for $R_3$, for example, particularly worth mentioning are acetyl, propionyl, butyryl, and benzoyl.

Aliphatic groups $R_5$ include straight-chain and branched, saturated and unsaturated residues, e.g., alkyl or alkenyl, preferably saturated ones, of 1–10, especially 1–6 carbon atoms, which can optionally be substituted by optionally substituted aryl and by halo. The optionally substituted aryl groups are those described for $R_2$. Examples include methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl, etc. If $R_5$ is halosubstituted, e.g., halosubstituted alkyl suitable halogens are fluorine, chlorine, and bromine and there usually are 1–3 such substituents.

The cycloalkyl group $R_5$ can contain 3–10, preferably 3–6 carbon atoms in the ring. The rings can be substituted by alkyl groups of 1–4 carbon atoms. Examples include cyclopropyl, cyclobutyl, cyclopentyl, cyclohexyl, methylcyclohexyl, and adamantyl.

Substituted or unsubstituted aryl groups $R_5$ are those described above for $R_2$. Examples include phenyl, 1-naphthyl, and 2-naphthyl, each of which can be substituted by 1–3 halogen atoms, a phenyl group, 1–3 alkyl groups of respectively 1–4 carbon atoms, a chloromethyl, fluoromethyl, trifluoromethyl, carboxy, alkoxy, or hydroxy. Substitution in the 3- and 4-position on the phenyl ring is preferred, for example by fluorine, chlorine, alkoxy, or trifluoromethyl, or in the 4-position by hydroxy.

Suitable heterocyclic groups $R_5$ are also those listed for $R_2$, e.g., 5- and 6-membered heterocycles containing at least one hetero atom, preferably nitrogen, oxygen, or sulfur and preferably aromatic monocycles, the remainder of the atoms being C-atoms. Examples include 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, and others.

Suitable groups include straight chain or branched, saturated or unsaturated alkylene or alkenylene residues, preferably saturated ones, all of 1–10, especially 1–5 carbon atoms, which can optionally be substituted by 1–2 fluorine atoms. Examples include: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyltrimethylene, 1-methylene-ethylene, 1-methylenetetramethylene, etc.

Suitable for salt formation are inorganic and organic bases, all of which are familiar to those skilled in the art for the preparation of physiologically compatible salts. Examples include alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

Suitable alkyl groups $R_6$ and $R_7$ include straight-chain and branched, saturated alkyl residues of 1–6, especially 1–4 carbon atoms, such as those mentioned for $R_2$.

The present invention furthermore concerns a process for the preparation of the $\Delta^{8,9}$-prostane derivatives of Formula I of this invention, comprising conventionally reacting a conventional compound of Formula II

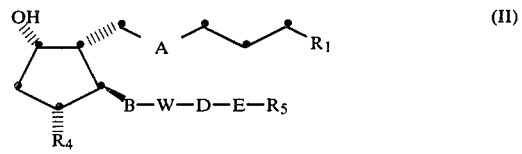

(II)

wherein
$R_1$ is

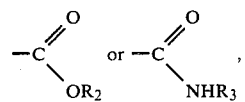

and

A, $R_4$, W, B, D, E, and $R_5$ are as defined above, and free OH-groups in $R_4$ and W are blocked, to form an intermediary 9-sulfonic acid ester and these reacting the latter with a base; and, if desired, subsequently, in any desired sequence, liberating blocked hydroxy groups and/or esterifying free hydroxy groups and/or hydrogenating or etherifying double bonds and/or saponifying an esterified carboxy group

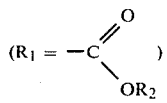

and/or esterifying a carboxy group ($R_2=H$) and/or converting a free carboxy group ($R_2=H$) into an amide

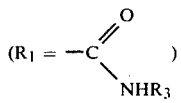

and/or reducing a free or esterified carboxy group

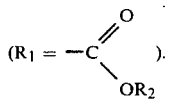

The reaction of the compounds of Formula II to obtain a 9-sulfonic acid ester can be conducted conventionally with an alkyl- or arylsulfonyl chloride or an alkyl- or arylsulfonic acid anhydride in the presence of an amine, e.g. pyridine, triethylamine, or DMAP (dimethylaminopyridine) at temperatures of $-60°$ C. to $+100°$ C., preferably at $-20°$ to $+50°$ C. The elimination of the 9-sulfonate takes place with a base, preferably tetrabutylammonium fluoride, in an inert solvent such as, for example, dimethylformamide, dimethylacetamide, hexamethylphosphoric triamide, dimethyl sulfoxide, dimethoxyethane, tetrahydrofuran, etc., at a temperatures of $0°$ to $100°$ C., preferably $20°-80°$ C.

Suitable alkyl or aryl groups in the sulfonyl chlorides or sulfonic acid anhydrides include those from p-toluene, methane, ethane, benzene, p-chloro-benzene, phenylmethane, isopropan, butane, isobutane.

The conventional reduction to prepare compounds of Formula I with $R_1$ as —$CH_2OH$— is carried out with a reducing agent suitable for the reduction of esters or carboxylic acids, such as, for example, lithium aluminum hydride, diisobutyl aluminum hydride, etc. Suitable solvents include diethyl ether, tetrahydrofuran, dimethoxyethane, toluene, etc. The reduction is conducted at temperatures from $-30°$ C. to the boiling temperature of the solvent employed, preferably at $0°-30°$ C.

The functionally modified hydroxy groups are also liberated by known methods. For example, hydroxy blocking groups, such as the tetrahydropyranyl residue, can be split off in an aqueous solution of an organic acid, e.g. oxalic acid, acetic acid, propionic acid, and others, or in an aqueous solution of an inorganic acid, e.g. hydrochloric acid. To improve solubility, a water-miscible, inert organic solvent is advantageously added. Suitable organic solvents include, for example, alcohols, such as methanol and ethanol, and ethers, such as dimethoxyethane, dioxane, and tetrahydrofuran. The preferred solvent is tetrahydrofuran. The splittine-off step is preferably effected at temperatures of $20°$ to $80°$ C.

The acyl groups are conventionally saponified, for example, with alkali metal or alkaline earth metal carbonates or hydroxides, in an alcohol or in the aqueous solution of an alcohol. Suitable alcohols include aliphatic alcohols, such as, for example, methanol, ethanol, butanol, etc., preferably methanol. Typical alkali metal carbonates and hydroxides are potassium and sodium salts. The potassium salts are preferred.

Examples of suitable alkaline earth metal carbonates and hydroxides are calcium carbonate, calcium hydroxide, and barium carbonate. The reaction takes place at $-10°$ to $+70°$ C., preferably at $+25°$ C.

The ester group

for $R_1$, wherein $R_2$ is an alkyl group of 1–10 carbon atoms, is conventionally introduced by means of methods known to those skilled in the art. The 1-carboxy compounds can be reacted, for example, with diazo hydrocarbons in a manner known per se. Esterification with diazo hydrocarbons takes place, for example, by mixing a solution of the diazo hydrocarbon in an inert solvent, preferably in diethyl ether, with the 1-carboxy compound in the same or in another inert solvent, such as methylene chloride, for example. After the reaction has been completed in 1–30 minutes, the solvent is removed and the ester purified as usual. Diazoalkanes are either known or can be produced according to conventional methods [Org. Reactions 8: 389–394 (1954).

The conventional introduction of the ester group

for $R_1$, wherein $R_2$ is a substituted or unsubstituted aryl group, takes place by means of methods known to persons skilled in the art. For example, the 1-carboxy compounds can be reacted with the corresponding arylhydroxy compounds with dicyclohexylcarbodiimide in the presence of a suitable base, e.g. pyridine, or triethylamine, in an inert solvent. Solvents suitable for this purpose are methylene chloride, ethylene chloride, chloroform, ethyl acetate, tetrahydrofuran, preferably chloroform. The reaction is carried out at temperatures of $-30°$ to $+50°$ C., preferably at $10°$ C.

The analogous compounds wherein $R_2$ is cycloalkyl or a heterocyclic residue can be prepared analogously to the techniques mentioned above.

If any $C\!=\!C$-double bonds present in the primary product are to be reduced, the hydrogenation is conducted by conventional methods.

The 5,6-double bond can be conventionally hydrogenated at low temperatures, preferably at about $-20°$ C., in a hydrogen atmosphere in the presence of a noble metal catalyst. A suitable catalyst is, for example, 10% palladium on carbon.

If the 5,6- as well as the 13,14-double bonds are hydrogenated, the process is carried out at a higher temperature, preferably at about $20°$ C.

The prostaglandin derivatives of Formula I wherein $R_2$ is a hydrogen atom can be converted into a salt with suitable amounts of the corresponding inorganic bases, under conventional neutralization conditions. For example, the solid inorganic salt is obtained when dissolving the corresponding PG acids in water containing the stoichiometric quantity of the base, after evaporation of the water or after adding a water-miscible solvent, e.g. alcohol or acetone.

For the production of an amine salt, which also takes place in the usual conventional way, the PG acid is dissolved, for example, in a suitable solvent, e.g. ethanol, acetone, diethyl ether, acetonitrile, or benzene, and at least the stoichiometric amount of the amine is added to this solution. In this process, the salt is ordinarily obtained in the solid form or is conventionally isolated after evaporation of the solvent.

The introduction of the amide group

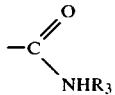

for $R_1$ takes place by using methods known to those skilled in the art. The carboxylic acids of Formula I ($R_2$=H) are first converted into the mixed anhydride in the presence of a tertiary amine, e.g. triethylamine, with isobutyl chloroformate. The mixed anhydride is reacted with the alkali salt of the corresponding amide or with ammonia ($R_3$=H) in an inert solvent or solvent mixture, such as, for example, tetrahydrofuran, dimethoxyethane, dimethylformamide, hexamethylphosphoric triamide, at temperatures of $-30°$ to $+60°$ C., preferably at $0°$–$30°$ C.

Another method for introducing the amide group

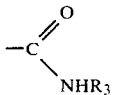

for $R_1$ resides in conventionally reacting a 1-carboxylic acid of Formula I ($R_2$=H) wherein free hydroxy groups are optionally blocked intermediarily, with compounds of Formula III

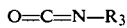

wherein $R_3$ has the meanings given above.

The reaction of the compound of Formula I ($R_2$=H) with an isocyanate of Formula III likewise takes place with the addition of a tertiary amine, e.g. triethylamine or pyridine. The reaction can be conducted without a solvent or in an inert solvent, preferably acetonitrile, tetrahydrofuran, acetone, dimethylacetamide, methylene chloride, diethyl ether, toluene, etc, at temperatures of $-80°$ to $100°$ C., preferably at $0°$–$30°$ C.

If the starting compound contains OH-groups in the prostane residue, these OH-groups also react. If, in the final analysis, end products are desired which contain free hydroxy groups in the prostane residue, it is advantageous to start with compounds wherein these groups are intermediarily blocked by ether or acyl residues which preferably can be readily split off.

The starting compounds of Formula II are all known compounds and/or are preparable from known starting materials, for example, by conventionally reducing a ketone of Formula IV

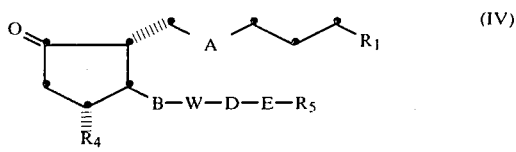

wherein
$R_1$ is

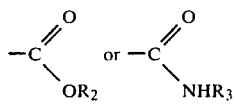

and A, B, W, D, E, and $R_5$ are as defined above, and free OH-groups in $R_4$ and W are blocked, with sodium borohydride, lithium tris(tert-butoxy)aluminum hydride, etc., and, optionally, subsequently, conventionally separating the epimeric $9\alpha$- and $9\beta$-positioned hydroxy compounds of Formula II.

The compounds of formula IV are all well known or conventionally prepared from known starting materials.

As compared with PGE derivatives, the novel $\Delta^{8,9}$-prostaglandins of this invention are distinguished by a higher stability.

The novel $\Delta^{8,9}$-prostane derivatives of Formula I are valuable pharmaceuticals for administration to mammals including humans, since they exhibit, with a similar spectrum of activity, a substantially improved higher specificity and, above all, considerably longer efficacy than the corresponding natural prostaglandins.

The novel prostaglandin analogs of this invention act strongly luteolytically, i.e. to trigger luteolysis, substantially smaller doses are required than in case of the corresponding natural prostaglandins.

Also for triggering abortions, especially upon oral or intravaginal administration, considerably lesser quantities of the novel prostaglandin analogs are necessary as compared with the natural prostaglandins.

When recording the isotonic uterine contraction of anesthetized rats and on the isolated rat uterus, it is found that the compounds of this invention are substantially more efficacious and that their effects are of a longer duration than in the case of the natural prostaglandins.

The novel prostaglandin derivatives are suitable, after a single enteral or parenteral administration, for inducing menstruation or interrupting pregnancy. They are furthermore suitable for synchronizing the sexual cycle in female mammals, such as rabbits, cattle, horses, pigs, etc. Furthermore, the prostaglandin derivatives of the present invention are suitable for cervix dilation as a preparation for diagnostic or therapeutic interventions.

The high tissue specificity of the compounds of this invention with antifertility activity is demonstrated in studies on other smooth-muscle organs, e.g. on the guinea pig ileum or on the isolated rabbit trachea, where a substantially lesser stimulation can be observed than caused by the natural prostaglandins. The compounds of this invention also have a bronchospasmolytic activity. Besides, they reduce swelling of the nasal mucous membrane.

The active agents of this invention inhibit gastric acid secretion, show a cytoprotective and ulcer-healing effect, and thus counteract the undesirable consequences of nonsteroidal anti-inflammatory agents (prostaglandin systhesis-inhibitors).

Several of the compounds show blood-pressure-lowering effects, a regulating effect on cardiac arrhythmias, and an inhibitory effect on platelet aggregation, with the ensuing conventional usage possibilities. Especially compounds with the structural features 16-aryloxy, 16-methyl or 16,16-dimethyl show the mentioned effects.

For medical use, the active agents can be fully conventionally converted into a form suitable for inhalant, oral, parenteral, or local (e.g. vaginal) administration. Aerosol solutions are suitably prepared for inhalation purposes. Tablets, dragees, or capsules are suitable for oral administration, for example. Sterile, injectable aqueous or oily solutions are utilized for parenteral administration. Suppositories are suitable and customary, for example, for vaginal administration.

Consequently, the invention also concerns medicinal agents containing the compounds of Formula I and customary auxiliary agents and excipients.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elexir or the like can be used wherein a sweetened vehicle is employed. Sustained release compositions can be formulated including those wherein the active compound is protected with differentially degradable coatings, e.g., by microencapsulation, multiple coatings, etc.

The dosage of the compounds according to this invention is usually 1–1500 μg/kg/day when administered to human patients as drugs for the treatment of the mentioned diseases.

The active agents of this invention can thus be utilized, in conjunction with such auxiliary compounds known and customary in galenic pharmacy, for example to produce preparations for triggering abortion, for cycle regulation, for induction of labor, or for the treatment of hypertonia. For this purpose, and also for the other applications, the preparations can contain 0.01–50 mg of the active compound.

Without further elaboration, it is believed that one skilled in the art can, using the preceding description, utilize the present invention to its fullest extent. The following preferred specific embodiments are, therefore, not to be limitative of the remainder of the disclosure in any way whatsoever.

In the following examples, all temperatures are set forth uncorrected in degrees Celsius; unless otherwise indicated, all parts and percentages are by weight.

EXAMPLE 1

(5Z,13E)-(11R,15R)-11,15-Dihydroxy-16-phenoxy-17,18,19,20-tetranor-5,8,13-prostatrienoic Acid Methyl Ester At 0° C., 1.9 g of p-toluenesulfonic acid chloride is added to a solution of 2.85 g of (5Z,13E)-(9S,11R,15R)-9-hydroxy-11,15-bis(tetrahydropyran-2-yloxy)-16-phenoxy-17,18,19,20-tetranor-5,13-prostadienoic acid methyl ester (prepared from the corresponding acid in methylene chloride with 0.5-molar ethereal diazomethane solution at 0° C.) in 9 ml of pyridine; the mixture is stirred for 16 hours at ice bath temperature and for 48 hours at 20° C. Then the mixture is combined with 6 ml of water, agitated for 3 hours at 20° C., diluted with ether, shaken in succession with water, 5% sulfuric acid, 5% sodium bicarbonate solution, and water, dried over magnesium sulfate, and evaporated under vacuum.

Yield: 3.3 g of the 9-tosylate as a colorless oil.

IR: 2950, 2875, 1734, 1600, 1590, 1496, 1365, 1240, 974 cm$^{-1}$.

A solution of 3.3 g of the above-obtained 9-tosylate in 90 ml of absolute tetrahydrofuran is combined with 6 g of tetrabutylammonium fluroide and agitated for 3 hours at 22° C. under argon. The mixture is thereafter diluted with 300 ml of ether, shaken three times with water, dried over magnesium sulfate, and evaporated under vacuum. The residue is purified by chromatography on silica gel. With hexane/ether (4+1), 1.8 g of (5Z,13E)-(11R,15R)-11,15-bis(tetrahydropyran-2-yloxy)-16-phenoxy-17,18,19,20-tetranor-5,8,13-prostatrienoic acid methyl ester is obtained as a colorless oil.

IR: 2960, 2855, 1730, 1600, 1588, 1495, 970 cm$^{-1}$.

To split off the blocking groups, 1.8 g of the $\Delta^{8,9}$-compound produced above is stirred for 16 hours at 22° C. with 60 ml of a mixture of acetic acid, water, and tetrahydrofuran (65+35+10) and thereafter evaporated under vacuum. The residue is purified by chromatography on silica gel. With ether as the eluent, 0.95 g of the title compound is obtained as a colorless oil.

IR: 3600, 3420 (broad), 2930, 2855, 1730, 1600, 1588, 971 cm$^{-1}$.

EXAMPLE 2

(13E)-(11R,15R)-11,15-Dihydroxy-16-phenoxy-17,18,19,20-tetranor-8,13-prostadienoic Acid Methyl Ester In analogy to Example 1, 1.35 g of (13E)-(9S,11R,15R)-9-hydroxy-11,15-bis(tetrahydropyran-2-yloxy)-16-phenoxy-17,18,19,20-tetranor-13-prostenoic acid methyl ester yields 800 mg of (13E)-(11R,15R)-11,15-bis(tetrahydropyran-2-yloxy)-16-phenoxy-17,18,19,20-tetranor-8,13-prostadienoic acid methyl ester as a colorless oil.

IR: 2960, 2858, 1730, 1600, 1588, 1496, 972 cm$^{-1}$.

After splitting off the blocking groups according to Example 1, 0.4 g of the title compound is obtained as a colorless oil.

IR: 3610, 3400 (broad), 2930, 2856, 1730, 1600, 1588, 972 cm$^{-1}$.

1H-NMR (CDCl$_3$): δ=3.68(3)s

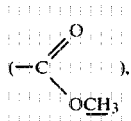

5.36(1)q(I=4 Hz,H-9), 4.09–4.29(1)m(H-11), 5.63–5.71(2) (H-13,14), 4.44–4.62(1)m(H-15), 3.78–4.04(2)m(H-16), 6.87–7.40(5)m(arom.H).

EXAMPLE 3

(13E)-(11R,15R)-11,15-Dihydroxy-16-(m-chlorophenoxy)-17,18,19,20-tetranor-8,13-prostadienoic Acid Methyl Ester In analogy to Example 1, 0.6 g of (13E)-(9S,11R,15R)-9-hydroxy-11,15-bis(tetrahydropyran-2-yloxy)-16-(m-chlorophenoxy)-17,18,19,20-tetranor-13-prostenoic acid methyl ester yields 0.35 g of (13E)-(11R,15R)-11,15-bis-(tetrahydropyran-2-yloxy)-16-(m-chlorophenoxy)-17,18,19,20-tetranor-8,13-prostadienoic acid methyl ester as an oil.

IR: 2958, 2860, 1730, 1600, 1588, 970 cm$^{-1}$.

After the blocking groups have been split off according to Example 1, 0.2 g of the title compound is obtained as a colorless oil.

IR: 3600, 3410 (broad), 2930, 2855, 1731, 1600, 1588, 972 cm$^{-1}$.

EXAMPLE 4

(5Z,13E)-(11R,15R)-11,15-Dihydroxy-16,16-dimethyl-5,8,13-prostatrienoic Acid Methyl Ester Analogously to Example 1, 2.75 g of (5Z,13E)-(9S,11R,15R)-11,15-bis(tetrahydropyran-2-yloxy)-16,16-dimethyl-9-hydroxy-5,13-prostadienoic acid methyl ester yields 1.6 g of (5Z,13E)-(11R,15R)-16,16-dimethyl-11,15-bis(tetrahydropyran-2-yloxy)-5,8,13-prostatrienoic acid methyl ester as a colorless oil.

IR: 2960, 2855, 1732, 975 cm$^{-1}$.

After the blocking groups have been split off as described in Example 1, 0.8 g of the title compound is obtained as a colorless oil.

IR: 3610, 3400 (broad), 2940, 2850, 1732, 975 cm$^{-1}$.

EXAMPLE 5

(13E)-(11R,15R)-11,15-Dihydroxy-16,16-dimethyl-8,13-prostadienoic Acid Methyl Ester Analogously to Example 1, 300 mg of (13E)-(9S,11R,15R)-11,15-bis(tetrahydropyran-2-yloxy)-16,16-dimethyl-9-hydroxy-13-prostenoic acid methyl ester yields 170 mg of (13E)-(11R,15R)-16,16-dimethyl-11,15-bis(tetrahydropyran-2-yloxy)-8,13-prostadienoic acid methyl ester as a colorless oil.

IR: 2955, 2860, 1732, 1495, 975 cm$^{-1}$.

After splitting off the blocking groups according to Example 1, 90 mg of the title compound is produced as a colorless oil.

IR: 3600, 3410 (broad), 2940, 2855, 1732, 975 cm$^{-1}$.

EXAMPLE 6

(5Z,13E)-(11R,16RS)-11,15α-Dihydroxy-16-methyl-5,8,13-prostatrienoic Acid Methyl Ester In analogy to Example 1, 1.4 g of (5Z,13E)-(9S,11R,16RS)-11,15α-bis(tetrahydropyran-2-yloxy)-9-hydroxy-16-methyl-5,13-prostadienoic acid methyl ester produces 0.85 g of (5Z,13E)-(11R,16RS)-11,15α-bis(tetrahydropyran-2-yloxy)-16-methyl-5,8,13-prostatrienoic acid methyl ester as a colorless oil.

IR: 2960, 2655, 1730, 1495, 974 cm$^{-1}$.

After splitting off the blocking groups according to Example 1, 0.5 g of the title compound is obtained as a colorless oil.

IR: 3610, 3400 (broad), 2935, 2855, 1730, 974 cm$^{-1}$.

EXAMPLE 7

(5Z,13E)-(11R,15RS)-11,15-Dihydroxy-15-methyl-5,8,13-prostatrienoic Acid Methyl Ester In analogy to Example 1, 0.65 g of (5Z,13E)-(9S,11R,15RS)-11,15-bis(tetrahydropyran-2-yloxy)-9-hydroxy-15-methyl-5,13-prostadienoic acid methyl ester yields 0.35 g of (5Z,13E)-(11R,15RS)-11,15-bis(tetrahydropyran-2-yloxy)-15-methyl-5,8,13-prostatrienoic acid methyl ester as a colorless oil.

IR: 1732, 970 cm$^{-1}$.

After splitting off the blocking groups as disclosed in Example 1, 0.26 g of the title compound is obtained as a colorless oil.

IR: 3600, 3420 (broad), 2932, 2856, 1732, 970 cm$^{-1}$.

EXAMPLE 8

(5Z,13E)-(11R,15R,16RS)-11,15-Dihydroxy-16-fluoro-5,8,13-prostatrienoic Acid Methyl Ester Analogously to Example 1, 0.8 g of (5Z,13E)-(9S,11R,15R,16RS)-11,15-bis(tetrahydropyran-2-yloxy)-9-hydroxy-16-fluoro-5,13-prostadienoic acid methyl ester yields 0.50 g of (5Z,13E)-(11R,15R,16RS)-11,15-bis(tetrahydropyran-2-yloxy)-16-fluoro-5,8,13-prostatrienoic acid methyl ester as a colorless oil.

IR: 2958, 1735, 976 cm$^{-1}$.

After the blocking groups have been split off according to Example 1, 0.29 g of the title compound is obtained as an oil.

IR: 3610, 3400 (broad), 2930, 2857, 1735, 976 cm$^{-1}$.

EXAMPLE 9

(5Z,13E)-(11R,16RS)-11,15α-Dihydroxy-16,19-dimethyl-5,8,13,18-prostatetraenoic Acid Methyl Ester In analogy to Example 1, 2.4 g of (5Z,13E)-(9S,11R,16RS)-11,15α-bis(tetrahydropyran-2-yloxy)-9-hydroxy-16,19-dimethyl-5,13,18-prostatrienoic acid methyl ester yields 1.5 g of (5Z,13E)-(11R,16RS)-11,15α-bis(tetrahydropyran-2-yloxy)-16,19-dimethyl-5,8,13,18-prostatetraenoic acid methyl ester as a colorless oil.

IR: 2960, 1732, 972 cm$^{-1}$.

After splitting off the blocking groups according to Example 1, 0.78 g of the title compound is produced as a colorless oil.

IR: 3600, 3400, 2932, 2855, 1732, 972 cm$^{-1}$.

EXAMPLE 10

(13E)-(11R,16RS)-11,15α-Dihydroxy-16,19-dimethyl-8,13-18-prostatrienoic Acid Methyl Ester Analogously to Example 1, 600 mg of (13E)-(9S,11R,16RS)-11,15α-bis(tetrahydropyran-2-yloxy)-9-hydroxy-16,19-dimethyl-13,18-prostadienoic acid methyl ester yields 350 mg of (13E)-(11R,16RS)-11,15α-bis(tetrahydropyran-2-yloxy)-16,19-dimethyl-8,13,18-prostatrienoic acid methyl ester as a colorless oil.

IR: 2962, 1731, 972 cm$^{-1}$.

After splitting off the blocking groups according to Example 1, 180 mg of the title compound is obtained as a colorless oil.

IR: 3610, 3410 (broad), 2930, 2855, 1731, 972 cm$^{-1}$.

EXAMPLE 11

(5Z,13E)-(11R,15R)-11,15-Dihydroxy-16,16,19-trimethyl-5,8,13,18-prostatetraenoic Acid Methyl Ester In analogy to Example 1, 1.35 g of (5Z,13E)-(9S,11R,15R)-11,15-bis(tetrahydropyran-2-yloxy)-9-hydroxy-16,16,19-trimethyl-5,13,18-prostatrienoic acid methyl ester yields 0.75 g of (5Z,13E)-(11R,15R)-11,15-bis(tetrahydropyran-2-yloxy)-16,16,19-trimethyl-5,8,13,18-prostatetraenoic acid methyl ester as a colorless oil.

IR: 2960, 2855, 1732, 974 cm$^{-1}$.

After splitting off the blocking groups as described in Example 1, 0.4 g of the title compound is obtained as a colorless oil.

IR: 3600, 3400 (broad), 2942, 2850, 1732, 974 cm$^{-1}$.

EXAMPLE 12

(13E)-(11R,15R)-11,15-Dihydroxy-16,16,19-trimethyl-8,13,18-prostatrienoic Acid Methyl Ester Analogously to Example 1, 600 mg of (13E)-(9S,11R,15R)-11,15-bis(tetrahydropyran-2-yloxy)-9-hydroxy-16,16,19-trimethyl-13,18-prostadienoic acid methyl ester produces 330 mg of (13E)-(11R,15R)-11,15-bis(tetrahydropyran-2-yloxy)-16,16,19-trimethyl-8,13,18-prostatrienoic acid methyl ester as a colorless oil.

IR: 2962, 2853, 1733, 974 cm$^{-1}$.

After splitting off the blocking groups according to Example 1, 185 mg of the title compound is obtained as a colorless oil.

IR: 3610, 3400 (broad), 2940, 2855, 1733, 974 cm$^{-1}$.

EXAMPLE 13

(13E)-(11R,15S)-11,15-Dihydroxy-8,13-prostadienoic Acid Methyl Ester

In analogy to Example 1, 280 mg of (13E)-(9S,11R,15S)-11,15-bis(tetrahydropyran-2-yloxy)-9-hydroxy-13-prostenoic acid methyl ester yields 170 mg of (13E)-(11R,15S)-11,15-bis(tetrahydropyran-2-yloxy)-8,13-prostadienoic acid methyl ester as a colorless oil.

IR: 2960, 2860, 1732, 976 cm$^{-1}$.

After splitting off the blocking groups according to Example 1, 90 mg of the title compound is produced as a colorless oil.

IR: 3600, 3410 (broad), 2930, 2855, 1732, 976 cm$^{-1}$.

EXAMPLE 14

(5Z,13E)-(11R,15R)-11,15-Dihydroxy-16-phenoxy-17,18,19,20-tetranor-5,8,13-prostatrienoic Acid 790 mg of the methyl ester prepared according to Example 1 is stirred for 5 hours with 20 ml of a solution of potassium hydroxide in ethanol and water (preparation: 2 g of potassium hydroxide is dissolved in 75 ml of ethanol and 25 ml of water). Thereafter the mixture is acidified with 10% citric acid solution to pH 4, extracted three times with methylene chloride, the organic extract is washed once with brine, dried over magnesium sulfate, and evaporated under vacuum. Chromatography of the residue in silica gel with methylene chloride/isopropanol (95+5) as eluent yields 610 mg of the title compound as a colorless oil.

IR: 3600, 3400 (broad), 2930, 2858, 1710, 1600, 1587, 1493, 970 cm$^{-1}$.

EXAMPLE 15

(13E)-(11R,15R)-11,15-Dihydroxy-16-phenoxy-17,18,19,20-tetranor-8,13-prostadienoic Acid Analogously to Example 14, 0.3 g of the methyl ester produced according to Example 2 yields 0.24 g of the title compound as an oil.

IR: 3600, 3410 (broad), 2935, 2856, 1710, 1600, 1590, 970 cm$^{-1}$.

EXAMPLE 16

(13E)-(11R,15R)-11,15-Dihydroxy-16-(m-chlorophenoxy)-17,18,19,20-tetranor-8,13-prostadienoic Acid In analogy to Example 14, 0.4 g of the methyl ester produced in Example 3 yields 0.36 g of the title compound as a colorless oil.

IR: 3600, 3400 (broad), 2930, 2856, 1710, 1598, 1588, 973 cm$^{-1}$.

EXAMPLE 17

(5Z,13E)-(11R,15R)-11,15-Dihydroxy-16,16-dimethyl-5,8,13-prostatrienoic Acid Analogously to Example 14, 0.45 g of the methyl ester prepared according to Example 4 yields 0.36 g of the title compound as a colorless oil.

IR: 3600, 3400 (broad), 2940, 2850, 1708, 974 cm$^{-1}$.

EXAMPLE 18

(13E)-(11R,15R)-11,15-Dihydroxy-16,16-dimethyl-8,13-prostadienoic Acid

Analogously to Example 14, 120 mg of the methyl ester produced as in Example 5 yields 95 mg of the title compound as a colorless oil.

IR: 3600, 3410 (broad), 2940, 2855, 1708, 974 cm$^{-1}$.

EXAMPLE 19

(5Z,13E)-(11R,16RS)-11,15α-Dihydroxy-16-methyl-5,8,13-prostatrienoic Acid

Analogously to Example 14, 0.25 g of the methyl ester prepared as described in Example 6 produces 0.2 g of the title compound as a colorless oil.

IR: 3600, 3400 (broad), 2935, 2855, 1710, 974 cm$^{-1}$.

EXAMPLE 20

(5Z,13E)-(11R,15RS)-11,15-Dihydroxy-15-methyl-5,8,13-prostatrienoic Acid

In analogy to Example 14, 0.2 g of the methyl ester prepared according to Example 7 yields 0.17 g of the title compound as a colorless oil.

IR: 3600, 3420 (broad), 2935, 2855, 1710, 972 cm$^{-1}$.

EXAMPLE 21

(5Z,13E)-(11R,15R,16RS)-11,15-Dihydroxy-16-fluoro-5,8,13-prostatrienoic Acid

In analogy to Example 14, 0.4 g of the methyl ester produced as described in Example 8 yields 0.3 g of the title compound as a colorless oil.

IR: 3610, 3400 (broad), 2930, 2855, 1709, 976 cm$^{-1}$.

EXAMPLE 22

(5Z,13E)-(11R,16RS)-11,15α-Dihydroxy-16,19-dimethyl-5,8,13,18-prostatetraenoic Acid Analogously to Example 14, 0.7 g of the methyl ester produced according to Example 9 yields 0.6 g of the title compound as a colorless oil.

IR: 3600, 3400 (broad), 2935, 2855, 1710, 972 cm$^{-1}$.

EXAMPLE 23

(13E)-(11R,16RS)-11,15α-Dihydroxy-16,19-dimethyl-8,13,18-prostatrienoic Acid

Analogously to Example 14, 0.45 g of the methyl ester produced according to Example 10 yields 0.38 g of the title compound as a colorless oil.

IR: 3600, 3410 (broad), 2930, 2855, 1710, 972 cm$^{-1}$.

EXAMPLE 24

(5Z,13E)-(11R,15R)-11,15-Dihydroxy-16,16,19-trimethyl-5,8,13,18-prostatetraenoic Acid Analogously to Example 14, 0.21 g of the methyl ester prepared according to Example 11 yields 0.17 g of the title compound as a colorless oil.

IR: 3600, 3410 (broad), 2940, 2850, 1709, 974 cm$^{-1}$.

EXAMPLE 25

(13E)-(11R,15R)-11,15-Dihydroxy-16,16,19-trimethyl-8,13,18-prostatrienoic Acid

Analogously to Example 14, 130 mg of the methyl ester produced by following Example 12 yields 110 mg of the title compound as a colorless oil.

IR: 3600, 3400 (broad), 2940, 2855, 1708, 974 cm$^{-1}$.

EXAMPLE 26

(5Z,13E)-(11R,15R)-1,11,15-Trihydroxy-16-phenoxy-17,18,19,20-tetranor-5,8,13-prostatriene A solution of 200 mg of the methyl ester prepared according to Example 1 in 12 ml of tetrahydrofuran is combined at 0° C. with 300 mg of lithium aluminum hydride in incremental portions, stirred for 45 minutes at 0° C. and for 20 minutes at 20° C. under argon, and then the excess reagent is destroyed at 0° C. by the dropwise addition of ethyl acetate. The mixture is agitated for 5 minutes, 2 ml of water and 60 ml of ether are added, and the mixture is stirred for 3 hours at 20° C., then filtered, washed with ether, the filtrate dried with magnesium sulfate, and evaporated under vacuum. After chromatography of the residue on silica gel with ethyl acetate/hexane (4+1), 165 mg of the title compound is produced as a colorless oil.

IR: 3600, 3430 (broad), 3000, 2930, 2858, 1600, 1588, 1495, 972 cm$^{-1}$.

EXAMPLE 27

(13E)-(11R,15R)-1,11,15-Trihydroxy-16-phenoxy-17,18,19,20-tetranor-8,13-prostadiene In analogy to Example 26, 180 mg of the methyl ester prepared according to Example 2 yields 155 mg of the title compound as a colorless oil.

IR: 3600, 3440 (broad), 3000, 2930, 2857, 1600, 1588, 1495, 972 cm$^{-1}$.

EXAMPLE 28

(5Z,13E)-(11R,15R)-1,11,15-Trihydroxy-16,16-dimethyl-5,8,13-prostatriene

Analogously to Example 26, 250 mg of the methyl ester prepared according to Example 4 yields 210 mg of the title compound as a colorless oil.

IR: 3600, 3415 (broad), 2935, 2956, 974 cm$^{-1}$.

EXAMPLE 29

(5Z,13E)-(11R,16RS)-16-Methyl-1,11,15α-trihydroxy-5,8,13-prostatriene

In analogy to Example 26, 140 mg of the methyl ester prepared according to Example 6 yields 110 mg of the title compound as a colorless oil.

IR: 3600, 3440 (broad), 2935, 2855, 973 cm$^{-1}$.

EXAMPLE 30

(5Z,13E)-(11R,16RS)-16,19-Dimethyl-1,11,15α-trihydroxy-5,8,13,18-prostatetraene

In analogy to Example 26, 220 mg of the methyl ester prepared according to Example 9 yields 180 mg of the title compound as a colorless oil.

IR: 3610, 3430 (broad), 2933, 2855, 972 cm$^{-1}$.

EXAMPLE 31

(13E)-(11R,16RS)-16,19-Dimethyl-1,11,15α-trihydroxy-8,13,18-prostatriene

In analogy to Example 26, 155 mg of the methyl ester prepared according to Example 10 yields 130 mg of the title compound as a colorless oil.

IR: 3600, 3430 (broad), 2933, 2855, 972 cm$^{-1}$.

EXAMPLE 32

(5Z,13E)-(11R,15R)-11,15-Dihydroxy-16-phenoxy-17,18,19,20-tetranor-5,8,13-prostatrienoic Acid Methylsulfonamide At 0° C., 90 mg of isobutyl chloroformate and 70 mg of triethylamine are added to a solution of 200 mg of (5Z,13E)-(11R,15R)-11,15-dihydroxy-16-phenoxy-17,18,19,20-tetranor-5,8,13-prostatrienoic acid (prepared according to Example 14) in 5 ml of dimethylformamide. After 30 minutes, 300 mg of the sodium salt of methylsulfonamide (produced from methylsulfonamide and sodium methylate) and 2 ml of hexamethylphosphoric triamide are added and the mixture is stirred for 5 hours at 20° C. Subsequently, the mixture is diluted with citrate buffer (pH 4), extracted with ethyl acetate, and extract washed with brine, dried over magnesium sulfate, and evaporated under vacuum. After chromatography of the residue on silica gel with methylene chloride, 131 mg of the title compound is obtained as an oil.

IR: 3600, 3410, 2948, 2860, 1720, 1600, 1588, 976 cm$^{-1}$.

EXAMPLE 33

(13E)-(11R,15R)-11,15-Dihydroxy-16-phenoxy-17,18,19,20-tetranor-8,13-prostadienoic Acid Methylsulfonamide In analogy to Example 32, 150 mg of (13E)-(11R,15R)-11,15-dihydroxy-16-phenoxy-17,18,19,20-tetranor-8,13-prostadienoic acid (prepared according to Example 15) yields 95 mg of the title compound as an oil.

IR: 3600, 3410, 2952, 2860, 1722, 1600, 1589, 976 cm$^{-1}$.

EXAMPLE 34

(13E)-(11R,15R)-11,15-Dihydroxy-16,16-dimethyl-8,13-prostadienoic Acid Methylsulfonamide In analogy to Example 32, 200 mg of (13E)-(11R,15R)-11,15-dihydroxy-16,16-dimethyl-8,13-prostadienoic acid (prepared according to Example 18) yields 115 mg of the title compound as an oil.

IR: 3600, 3405 (broad), 2942, 2855, 1720, 974 cm$^{-1}$.

EXAMPLE 35

(13E)-(11R,16RS)-11,15α-Dihydroxy-16,19-dimethyl-8,13,18-prostatrienoic Acid Methylsulfonamide Analogously to Example 32, 200 mg of (13E)-(11R,16RS)-11,15α-dihydroxy-16,19-dimethyl-8,13,18-prostatrienoic acid (produced according to Example 23) yields 100 mg of the title compound as a colorless oil.

IR: 3600, 3410 (broad), 2943, 2860, 1722, 976 cm$^{-1}$.

EXAMPLE 36

(13E)-(11R,15R)-11,15-Dihydroxy-16-phenoxy-17,18,19,20-tetranor-8,13-prostadienoic Acid Isopropylsulfonamide 210 mg of (13E)-(11R,15R)-11,15-dihydroxy-16-phenoxy-17,18,19,20-tetranor-8,13-prostadienoic acid (prepared according to Example 15) is dissolved in 5 ml of dimethylformamide and combined at 0° C. with 80 mg of isobutyl chloroformate and 60 mg of triethylamine. After 30 minutes, 200 mg of the sodium salt of isopropylsulfonamide (prepared from isopropylsulfonamide and sodium methylate) and 2 ml of hexamethylphosphoric triamide are added thereto and the mixture is stirred for 3 hours at 25° C. To work up the reaction mixture, 100 ml of citrate buffer (pH 4) is added, the mixture extracted repeatedly with ethyl acetate, the organic phase washed with brine, dried over magnesium sulfate, and evaporated under vacuum. Chromatography of the residue on silica gel with methylene chloride yields 120 mg of the title compound as an oil.

IR: 3600, 3400, 2955, 2866, 1725, 1601, 1588, 1125, 976 cm$^{-1}$.

EXAMPLE 37

(13E)-(11R,15R)-11,15-Dihydroxy-16-phenoxy-17,18,19,20-tetranor-8,13-prostadienoic Acid Acetylamide A solution of 557 mg of (13E)-(11R,15R)-11,15-bis(-tetrahydropyran-2-yloxy)-16-phenoxy-17,18,19,20-tetranor-8,13-prostadienoic acid methyl ester (prepared according to Example 2) in 10 ml of methanol is stirred with 2 ml of 2N sodium hydroxide solution for 6 hours under argon. The mixture is concentrated under vacuum, diluted with 50 ml of brine, acidified with citric acid to pH 4.5, and extracted repeatedly with ethyl acetate. The organic extract is washed with brine, dried over magnesium sulfate, and evaporated under vacuum, thus obtaining as the residue 540 mg of (13E)-(11R,15R)-11,15-bis(tetrahydropyran-2-yloxy)-16-phenoxy-17,18,19,20-tetranor-8,13-prostadienoic acid.

To form the acetylamide, the acid is dissolved in 15 ml of acetonitrile, combined with 130 mg of triethylamine, and at 0° C. a solution of 102 mg of acetyl isocyanate in 10 ml of acetonitrile is added dropwise thereto. The mixture is stirred for 2 hours at 20° C., diluted with 100 ml of citrate buffer (pH 4), extracted several times with ether, the organic base is washed with brine, dried over magnesium sulfate, and evaporated under vacuum. To split off the blocking groups, the residue is stirred for 4 hours at 40° C. with 15 ml of glacial acetic acid/-water/tetrahydrofuran (65/35/10) and then evaporated to dryness under vacuum. The residue is chromatographed on silica gel with methylene chloride with the addition of 0.1–0.5% isopropyl alcohol, thus producing 200 mg of the title compound as an oil.

IR: 3600, 3405, 2948, 2860, 1710, 1600, 1588, 978 cm$^{-1}$.

EXAMPLE 38

(13E)-(11R,15R)-11,15-Dihydroxy-16-phenoxy-17,18,19,20-tetranor-8,13-prostadienoic Acid Amide A solution of 210 mg of (13E)-(11R,15R)-11,15-dihydroxy-16-phenoxy-17,18,19,20-tetranor-8,13-prostadienoic acid (produced according to Example 15) in 5 ml of tetrahydrofuran is combined with 80 mg of isobutyl chloroformate and 60 mg of triethylamine and stirred for one hour at 0° C. Then gaseous ammonia is introduced into the reaction mixture at 0° C. for 10 minutes, whereafter the mixture is left for one hour at 25° C. To work up the mixture, it is diluted with water, repeatedly extracted with methylene chloride, the extracts are shaken with brine, dried over magnesium sulfate, and evaporated under vacuum. For purifying purposes, the product is chromatographed on silica gel with methylene chloride/1% isopropyl alcohol, thus obtaining 130 mg of the title compound as an oil.

IR: 3600, 3540, 3410, 2960, 2858, 1665, 1600, 1588, 974 cm$^{-1}$.

EXAMPLE 39

(13E)-(11R,16RS)-11,15α-Dihydroxy-16,19-dimethyl-8,13,18-prostatrienoic Acid Amide In analogy to Example 38, 200 mg of (13E)-(11R,16RS)-11,15α-dihydroxy-16,19-dimethyl-8,13,18-prostatrienoic acid (prepared as described in Example 23) yields 110 mg of the title compound as an oil.

IR: 3600, 3450, 2962, 2848, 1668, 978 cm$^{-1}$.

EXAMPLE 40

(13E)-(11R,15R)-11,15-Dihydroxy-16-phenoxy-17,18,19,20-tetranor-8,13-prostadienoic Acid Tris(hydroxymethyl)aminomethane Salt At 65° C., a solution of 122 mg of tris(hydroxymethyl)aminomethane in 0.4 ml of water is added to a solution of 390 mg of (13E)-(11R,15R)-11,15-dihydroxy-16-phenoxy-17,18,19,20-tetranor-8,13-prostadienoic acid (prepared according to Example 15) in 70 ml of acetonitrile. The mixture is allowed to cool down to 20° C. under agitation, decanted from the solvent, and the residue is dried under vacuum, thus obtaining 320 mg of the title compound as a waxy mass.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A $\Delta^{8,9}$-prostane derivative of the formula

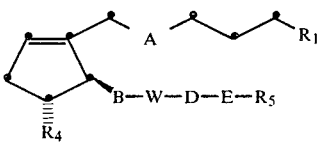

wherein
$R_1$ is $CH_2OH$ or

wherein $R_2$ is (a) hydrogen, (b) $C_{1-10}$ alkyl, (c) $C_{1-10}$ alkyl substituted by halogen; $C_{1-4}$ alkoxy; $C_{6-10}$-aryl or aroyl; $C_{6-10}$-aryl or aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5-6 ring atoms, one or two of which is O, N or S, the remainder being carbon atoms; or $R_1$ is

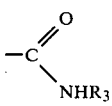

wherein $R_3$ is an acyl group of of a hydrocarbon $C_{1-15}$ carboxylic or sulfonic acid or is one of the $R_2$ groups;
A is $-CH_2-CH_2-$ or cis$-CH=CH-$;
B is $-CH_2-CH_2-$, trans$-CH=CH-$ or $-C\equiv C-$;
W is hydroxymethylene, RO—methylene,

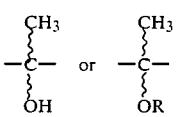

wherein all OH— or OR— groups are in the α- or β-position,
R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;
D and E jointly are a direct bond or
D is straight-chain or branched alkylene or alkenylene of 1-10 carbon atoms, optionally substituted by 1-2 fluorine atoms and E is oxygen, sulfur, a direct bond, $-C\equiv C-$, or $-CR_6=CR_7-$, wherein $R_6$ and $R_7$ differ from each other and each is hydrogen, chlorine or $C_{1-6}$-alkyl;
$R_4$ is OH or OR;
$R_5$ is (a) a $C_{1-10}$ hydrocarbon aliphatic radical, (b) a $C_{1-10}$ hydrocarbon aliphatic radical substituted by $C_{6-10}$-aryl or -aroyl or by $C_{6-10}$-aryl or -aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one or two of which is O, N or S, the remainder being carbon atoms; or when $R_2$ is hydrogen, a physiologically compatible salt thereof with a base with the proviso that D-E-$R_5$ is not n-pentyl, when W is —CHOR—, B is trans—CH=CH—, $R_4$ is OR, A is cis—CH=CH—, $R_1$ is —COOCH$_3$, and R is H or tetrahydropyranyl.

2. A compound of claim 1 wherein B-W-D-E-$R_5$ is

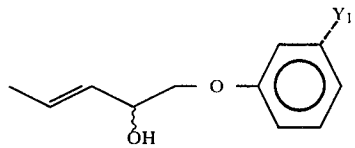

wherein $Y_1$ is halo or H.

3. A compound of claim 1 wherein B-W-D-E-$R_5$ is

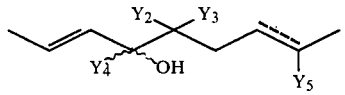

wherein each of $Y_2-Y_5$ independently is H or $CH_3$ and $Y_3$ can also be F; and ⩳ represents a single or double bond.

4. (5Z,13E)-(11R,15R)-11,15-Dihydroxy-16-phenoxy-17,18,19,20-tetranor-5,8,13-prostatrienoic acid methyl ester, a compound of claim 1.

5. (13E)-(11R,15R)-11,15-Dihydroxy-16-phenoxy-17,18,19,20-tetranor-8,13-prostadienoic acid methyl ester, a compound of claim 1.

6. (13E)-(11R,15R)-11,15-Dihydroxy-16-(m-chlorophenoxy)-17,18,19,20-tetranor-8,13-prostadienoic acid methyl ester, a compound of claim 1.

7. (5Z,13E)-(11R,15R)-11,15-Dihydroxy-16,16-dimethyl-5,8,13-prostatrienoic acid methyl ester, a compound of claim 1.

8. (13E)-(11R,15R)-11,15-Dihydroxy-16,16-dimethyl-8,13-prostadienoic acid methyl ester, a compound of claim 1.

9. (5Z,13E)-(11R,16RS)-11,15α-Dihydroxy-16-methyl-5,8,13-prostatrienoic acid methyl ester, a compound of claim 1.

10. (5Z,13E)-(11R,15RS)-11,15-Dihydroxy-15-methyl-5,8,13-prostatrienoic acid methyl ester, a compound of claim 1.

11. (5Z,13E)-(11R,15R,16RS)-11,15-Dihydroxy-16-fluoro-5,8,13-prostatrienoic acid methyl ester, a compound of claim 1.

12. (5Z,13E)-(11R,16RS)-11,15α-Dihydroxy-16,19-dimethyl-5,8,13,18-prostatetraenoic acid methyl ester, a compound of claim 1.

13. (13E)-(11R,16RS)-11,15α-Dihydroxy-16,19-dimethyl-8,13,18-prostatrienoic acid methyl ester, a compound of claim 1.

14. (5Z,13E)-(11R,15R)-11,15-Dihydroxy-16,16,19-trimethyl-5,8,13,18-prostatetraenoic acid methyl ester, a compound of claim 1.

15. (13E)-(11R,15R)-11,15-Dihydroxy-16,16,19-trimethyl-8,13,18-prostatrienoic acid methyl ester, a compound of claim 1.

16. (13E)-(11R,15S)-11,15-Dihydroxy-8,13-prostadienoic acid methyl ester, a compound of claim 1.

17. (5Z,13E)-(11R,15R)-11,15-Dihydroxy-16-phenoxy-17,18,19,20-tetranor-5,8,13-prostatrienoic acid, a compound of claim 1.

18. (13E)-(11R,15R)-11,15-Dihydroxy-16-phenoxy-17,18,19,20-tetranor-8,13-prostadienoic acid, a compound of claim 1.

19. (13E)-(11R,15R)-11,15-Dihydroxy-16-(m-chlorophenoxy)-17,18,19,20-tetranor-8,13-prostadienoic acid, a compound of claim 1.

20. (5Z,13E)-(11R,15R)-11,15-Dihydroxy-16,16-dimethyl-5,8,13-prostatrienoic acid, a compound of claim 1.

21. (13E)-(11R,15R)-11,15-Dihydroxy-16,16-dimethyl-8,13-prostadienoic acid, a compound of claim 1.

22. (5Z,13E)-(11R,16RS)-11,15α-Dihydroxy-16-methyl-5,8,13-prostatrienoic acid, a compound of claim 1.

23. (5Z,13E)-(11R,15RS)-11,15-Dihydroxy-15-methyl-5,8,13-prostatrienoic acid, a compound of claim 1.

24. (5Z,13E)-(11R,15R,16RS)-11,15-Dihydroxy-16-fluoro-5,8,13-prostatrienoic acid, a compound of claim 1.

25. (5Z,13E)-(11R,16RS)-11,15α-Dihydroxy-16,19-dimethyl-5,8,13,18-prostatetraenoic acid, a compound of claim 1.

26. (13E)-(11R,16RS)-11,15α-Dihydroxy-16,19-dimethyl-8,13,18-prostatrienoic acid, a compound of claim 1.

27. (5Z,13E)-(11R,15R)-11,15-Dihydroxy-16,16,19-trimethyl-5,8,13,18-prostatetraenoic acid, a compound of claim 1.

28. (13E)-(11R,15R)-11,15-Dihydroxy-16,16,19-trimethyl-8,13,18-prostatrienoic acid, a compound of claim 1.

29. (5Z,13E)-(11R,15R)-1,11,15-Trihydroxy-16-phenoxy-17,18,19,20-tetranor-5,8,13-prostatriene, a compound of claim 1.

30. (13E)-(11R,15R)-1,11,15-Trihydroxy-16-phenoxy-17,18,19,20-tetranor-8,13-prostadiene, a compound of claim 1.

31. (5Z,13E)-(11R,15R)-1,11,15-Trihydroxy-16,16-dimethyl-5,8,13-prostatriene, a compound of claim 1.

32. (5Z,13E)-(11R,16RS)-16-Methyl-1,11,15α-trihydroxy-5,8,13-prostatriene, a compound of claim 1.

33. (5Z,13E)-(11R,16RS)-16,19-Dimethyl-1,11,15α-trihydroxy-5,8,13,18-prostatetraene, a compound of claim 1.

34. (13E)-(11R,16RS)-16,19-Dimethyl-1,11,15α-trihydroxy-8,13,18-prostatriene, a compound of claim 1.

35. (5Z,13E)-(11R,15R)-11,15-Dihydroxy-16-phenoxy-17,18,19,20-tetranor-5,8,13-prostatrienoic acid methylsulfonamide, a compound of claim 1.

36. (13E)-(11R,15R)-11,15-Dihydroxy-16-phenoxy-17,18,19,20-tetranor-8,13-prostadienoic acid methylsulfonamide, a compound of claim 1.

37. (13E)-(11R,15R)-11,15-Dihydroxy-16,16-dimethyl-8,13-prostadienoic acid methylsulfonamide, a compound of claim 1.

38. (13E)-(11R,16RS)-11,15α-Dihydroxy-16,19-dimethyl-8,13,18-prostatrienoic acid methylsulfonamide, a compound of claim 1.

39. (13E)-(11R,15R)-11,15-Dihydroxy-16-phenoxy-17,18,19,20-tetranor-8,13-prostadienoic acid isopropylsulfonamide, a compound of claim 1.

40. (13E)-(11R,15R)-11,15-Dihydroxy-16-phenoxy-17,18,19,20-tetranor-8,13-prostadienoic acid acetylamide, a compound of claim 1.

41. (13E)-(11R,15R)-11,15-Dihydroxy-16-phenoxy-17,18,19,20-tetranor-8,13-prostadienoic acid amide, a compound of claim 1.

42. (13E)-(11R,16RS)-11,15α-Dihydroxy-16,19-dimethyl-8,13,18-prostatrienoic acid amide, a compound of claim 1.

43. (13E)-(11R,15R)-11,15-Dihydroxy-16-phenoxy-17,18,19,20-tetranor-8,13-prostadienoic acid tris(hydroxymethyl)aminomethane salt, a compound of claim 1.

44. A pharmaceutical composition comprising an amount of a compound effective to trigger luteolysis and a pharmaceutically acceptable carrier, wherein the compound is a $\Delta^{8,9}$-prostane derivative of the formula

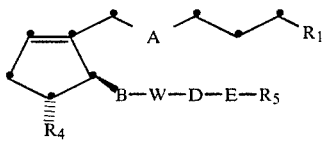

wherein
$R_1$ is $CH_2OH$ or $$-C\underset{OR_2}{\overset{\displaystyle O}{\diagup\!\!\!\diagdown}}$$

wherein $R_2$ is (a) hydrogen, (b) $C_{1-10}$ alkyl, (c) $C_{1-10}$ alkyl substituted by halogen; $C_{1-4}$ alkoxy; $C_{6-10}$-aryl or aroyl; $C_{6-10}$-aryl or aroyl each substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, or (h) an aromatic heterocycle of 5-6 ring atoms, one or two of which is O, N or S, the remainder being carbon atoms; or $R_1$ is

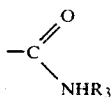

wherein $R_3$ is an acyl group of of a hydrocarbon $C_{1-15}$ carboxylic or sulfonic acid or is one of the $R_2$ groups;

A is —$CH_2$—$CH_2$— or cis—CH=CH—;

B is —$CH_2$—$CH_2$—, trans—CH=CH— or —C≡C—;

W is hydroxymethylene, RO-methylene,

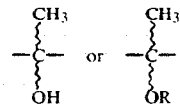

wherein all OH— or OR— groups are in the α- or β-position,

R is tetrahydropyranyl, tetrahydrofuranyl, α-ethoxyethyl, trimethylsilyl, dimethyl-tert-butylsilyl, tribenzylsilyl or an acyl group of a $C_{1-5}$-hydrocarbon carboxylic or sulfonic acid;

D and E jointly are a direct bond or

D is straight-chain or branched alkylene or alkenylene of 1-10 carbon atoms, optionally substituted by 1-2 fluorine atoms and E is oxygen, sulfur, a direct bond, —C≡C—, or —$CR_6$=$CR_7$—, wherein $R_6$ and $R_7$ differ from each other and each is hydrogen, chlorine or $C_{1-6}$-alkyl;

$R_4$ is OH or OR;

$R_5$ is (a) a $C_{1-10}$ hydrocarbon aliphatic radical, (b) a $C_{1-10}$ hydrocarbon aliphatic radical substituted by $C_{6-10}$-aryl or -aroyl or by $C_{6-10}$-aryl or -aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl; (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one or two of which is O, N or S, the remainder being carbon atoms; or when $R_2$ is hydrogen, a physiologically compatible salt thereof with a base.

45. A method of achieving a luteolytic effect in a patient in whom it is desired to achieve such an effect comprising administering to the patient an amount of a compound effective to trigger luteolysis wherein the compound is a $\Delta^{8,9}$-prostane derivative of the formula

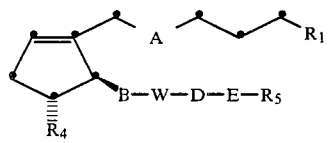

wherein $R_1$ is $CH_2OH$ or

wherein $R_2$ is (a) hydrogen, (b) $C_{1-10}$ alkyl, (c) $C_{1-10}$ alkyl substituted by halogen; $C_{1-4}$ alkoxy; $C_{6-10}$-aryl or aroyl; $C_{6-10}$-aryl or aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5-6 ring atoms, one or two of which is O, N or S, the remainder being carbon atoms; or $R_1$ is

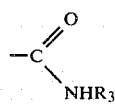

wherein $R_3$ is an acyl group of of a hydrocarbon $C_{1-15}$ carboxylic or sulfonic acid or is one of the $R_2$ groups;

A is —$CH_2$—$CH_2$— or cis—CH=CH—;

B is —$CH_2$—$CH_2$—, trans—CH=CH— or —C≡C—;

W is hydroxymethylene, RO-methylene,

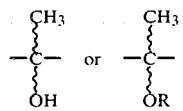

wherein all OH— or OR— groups are in the α- or β-position,

R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;

D and E jointly are a direct bond or

D is straight-chain or branched alkylene or alkenylene of 1-10 carbon atoms, optionally substituted by 1-2 fluorine atoms and E is oxygen, sulfur, a direct bond, —C≡C—, or —$CR_6$=$CR_7$—, wherein $R_6$ and $R_7$ differ from each other and each is hydrogen, chlorine or $C_{1-6}$-alkyl;

$R_4$ is OH or OR;

$R_5$ is (a) a $C_{1-10}$ hydrocarbon aliphatic radical, (b) a $C_{1-10}$ hydrocarbon aliphatic radical substituted by $C_{6-10}$-aryl or -aroyl or by $C_{6-10}$-aryl or -aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one or two of which is O, N or S, the remainder being carbon atoms; or when $R_2$ is hydrogen, a physiologically compatible salt thereof with a base.

46. A $\Delta^{8,9}$-prostane derivative of the formula

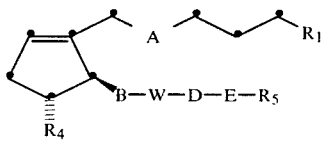

wherein
$R_1$ is $CH_2OH$ or

wherein $R_2$ is (a) hydrogen, (b) $C_{1-10}$ alkyl, (c) $C_{1-10}$ alkyl substituted by halogen; $C_{1-4}$ alkoxy; $C_{6-10}$-aryl or aroyl; $C_{6-10}$-aryl or aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5-6 ring atoms, one or two of which is O, N or S, the remainder being carbon atoms; or $R_1$ is

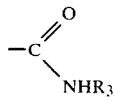

wherein $R_3$ is an acyl group of of a hydrocarbon $C_{1-5}$ carboxylic or sulfonic acid or is one of the $R_2$ groups;

A is $-CH_2-CH_2-$ or cis$-CH=CH-$;
B is $-CH_2-CH_2-$, trans$-CH=CH-$ or $-C\equiv C-$;
W is hydroxymethylene, RO-methylene,

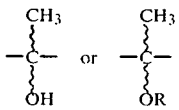

wherein all OH— or OR— groups are in the α- or β-position,
R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;
D and E jointly are a direct bond or
D is straight-chain or branched alkylene or alkenylene of 1-10 carbon atoms, optionally substituted by 1-2 fluorine atoms and E is oxygen, sulfur, a direct bond, $-C\equiv C-$, or $-CR_6=CR_7-$, wherein $R_6$ and $R_7$ differ from each other and each is hydrogen, chlorine or $C_{1-6}$-alkyl;
$R_4$ is OH or OR;
$R_5$ is (a) a $C_{1-10}$ hydrocarbon aliphatic radical, (b) a $C_{1-10}$ hydrocarbon aliphatic radical subsituted by $C_{6-10}$-aryl or -aroyl or by $C_{6-10}$-aryl or -aroyl each substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one or two of which is O, N or S, the remainder being carbon atoms; or when $R_2$ is hydrogen, a physiologically compatible salt thereof with a base, with the proviso that D-E-$R_5$ is not n-pentyl when B is trans$-CH=CH-$, A is cis$-CH=CH-$ and $R_1$ is $-COOR'$ wherein R' is H or alkyl.

* * * * *